United States Patent [19]

Kubotsu et al.

[11] Patent Number: 5,654,156

[45] Date of Patent: Aug. 5, 1997

[54] IMMUNOASSAY USING LIPOSOMES

[75] Inventors: Kazuhisa Kubotsu; Masaaki Kida; Sachiko Goto, all of Amagasaki, Japan

[73] Assignee: Wako Pure Chemical Industries, Ltd., Osaka, Japan

[21] Appl. No.: 264,754

[22] Filed: Jun. 23, 1994

Related U.S. Application Data

[63] Continuation of Ser. No. 5,260, Jan. 19, 1993, abandoned.

[30] Foreign Application Priority Data

Jan. 22, 1992 [JP] Japan .................................. 4-031591

[51] Int. Cl.$^6$ .................................................. G01N 33/53
[52] U.S. Cl. .................. 435/7.1; 435/184; 435/692; 436/821
[58] Field of Search .................. 435/7.1, 184, 962; 436/528, 821, 825, 829

[56] References Cited

U.S. PATENT DOCUMENTS

| | | | |
|---|---|---|---|
| 4,307,190 | 12/1981 | Masson et al. | 435/7 |
| 4,342,826 | 8/1982 | Cole | 435/7 |
| 4,703,001 | 10/1987 | Vodian et al. | 435/5 |
| 5,080,833 | 1/1992 | Ishimori | 260/408 |

FOREIGN PATENT DOCUMENTS

| | | |
|---|---|---|
| 63-231267 | 9/1988 | Japan . |
| 1-079661 | 3/1989 | Japan . |
| 1-214762 | 8/1989 | Japan . |
| 1-214763 | 8/1989 | Japan . |
| 1 503 821 | 8/1989 | U.S.S.R. . |
| 2 069 133 | 8/1981 | United Kingdom . |

OTHER PUBLICATIONS

Sam Franbel et al., Gradwhol's Chemical Laboratory Methods and Diagnosis, vol. 2, 7th ed. P1478, 1970.

*Primary Examiner*—James C. Housel
*Assistant Examiner*—Theresa King
*Attorney, Agent, or Firm*—Armstrong, Westerman, Hattori, McLeland & Naughton

[57] ABSTRACT

Complement immunoassay using liposomes is improved by pretreatment of a sample solution before determination of analyte comprising acidifying or alkalinizing the sample solution, followed by changing the pH to about neutral so as to remove influences caused by interfering substances present in the sample.

4 Claims, 2 Drawing Sheets

IMMUNOASSAY USING LIPOSOMES

This application is a continuation of application Ser. No. 08/005,260 filed Jan. 19, 1993, now abandoned.

BACKGROUND OF THE INVENTION

This invention relates to an improved immunoassay method applying a lysing action of complement for liposome membranes.

Immunoassay is a measuring method utilizing an antigen-antibody reaction. It is widely used as a method for specifically measuring trace components, for example, living components such as proteins, hormones, active peptides, autacoid, tumor maskers, immunoglobulin, etc., drugs such as digoxin, phenytoin, phenobarbital, etc., in body fluids.

As immunoassays which are now generally used, there are radioimmunoassay (RIA), enzyme immunoassay (EIA), etc. These methods permit quantitative measurement of trace components in samples but involve individual problems. That is, RIA is disadvantageous, for example, in that since radioisotopes should be used therein, RIA requires special facilities and troublesome disposal of wastes. EIA is disadvantageous, for example, in that it requires a relatively long measuring time and is difficult to apply to an autoanalyzer.

Therefore, as an immunoassay involving none of these problems, there has recently been proposed and noted an immunoassay using liposomes (hereinafter referred to as "liposome immunoassay"). A typical example of this method is disclosed in Japanese Patent Unexamined Publication No. 56-132564 (U.S. Pat. No. 4,342,826). This method comprises mixing liposomes, surfaces of which are fixed with an analyte to be measured and which encapsulate a marker (e.g. enzyme) therein, a sample and an antibody to an analyte to carry out the antigen-antibody reaction and adding complement thereto. Thus, complement activated by an antigen-antibody complex formed on the surfaces of liposomes, lyses liposome membranes to liberate the marker encapsulated. This liposome immunoassay using complement (hereinafter referred to as "complement immunoassay") does not include the above-mentioned problems of RIA and EIA and can conduct a series of reactions in a uniform reaction system, so that this method is noticed for carrying out the measurement simply and in a short time.

But according to the complement immunoassay, when a series of complement components and a complement controlling factor (ex. C1INE, C3BINA (Factor I), B1H (Factor H), etc.) are present in samples, the liposome lysing reaction by activation of complement is influenced so as to lose the correlation between the amount of an analyte in a sample and the amount of a marker released from liposomes. Thus, when serum or plasma is used as a sample, the released amount of marker is changed by complement activity by the influence of the above-mentioned interfering substance for the measurement contained in such a sample, resulting in failing to obtain precise measured values. In order to remove such an influence in the case of using serum or plasma as a sample, it is recommended to subject the sample to pretreatment, for example, heating at 56° C. for 30 minutes, or at 60° C. for 3 minutes. [Japanese Patent Unexamined Publication No. 1-214762; Gradwhol's Chemical Laboratory Methods and Diagnosis, vol 2, 7th Ed, San Frankel et al., p. 1478 (1970)]. But such a method requires complicated procedures and a longer time, in addition to inconvenience of vaporization of the sample by the heat. Further, it is difficult to apply such a heat treatment method to autoanalyzers now widely used for detection. Further, there is also proposed a method for adjusting the ionic strength of a buffer for reaction for the same purpose (Japanese Patent Unexamined Publication No. 1-214763). But according to this method, when a salt concentration becomes too high, there is a fear of influencing the antigen-antibody reaction.

SUMMARY OF THE PRESENT INVENTION

It is an object of the present invention to provide a process of an improved complement immunoassay which can be carried out simply, rapidly and precisely and can be applied to an autoanalyzer by removing an influence of substances contained in a sample and influencing the above-mentioned liposome lysing reaction. It is another object of the present invention to provide a reagent composition for carrying out such a process.

The present invention provide an immunoassay for determining the amount of analyte in a sample, using a reagent composition comprising.

(i) liposomes fixing an antigen or antibody to analyte on surfaces of liposome membranes, encapsulating a detectable marker therein, and being susceptible to membrane lysing action by complement activity, and (ii) complement characterized in that a sample solution before the determination is subjected to a pretreatment comprising temporarily acidifying the sample solution to pH 4.5 or lower or temporarily alkalinizing the sample solution to pH 11 or higher so as to remove influences caused by interfering substances present in the sample, and the pH of sample solution is changed to about neutral.

The present invention further provides a reagent composition for immunoassay comprising (i) liposomes fixing an antigen or antibody to analyte on surfaces of liposome membranes, encapsulating a detectable marker therein, and being susceptible to membrane lysing action by complement activity, (ii) complement, and (iii) a reagent for making a sample solution acidic with pH 4.5 or less or alkaline with pH 11 or higher temporarily.

DESCRIPTION OF THE PREFERRED EMBODIMENTS

Figure 1:
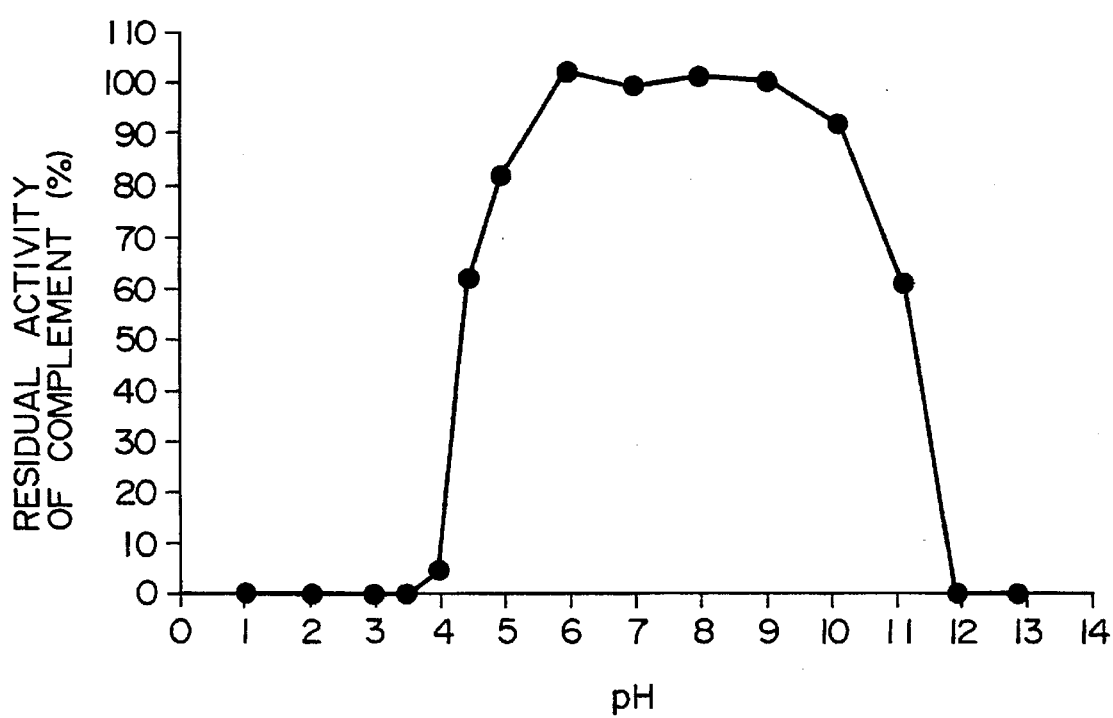
FIG. 1 is a graph showing a relationship between pH of a sample solution and residual activity of complement in relative values obtained in Experimental Example 1.

The process of the present invention is characterized by making a sample solution temporarily acidic with pH 4.5 or less or alkaline with pH 11 or higher so as to remove interference substances for the measurement present in the sample, and changing the pH of the sample solution to about neutral, before the measurement of the amount of analyte in the sample. The word "temporarily" is used in the present invention, because the pH of sample solution is afterward changed to about neutral.

As a reagent for temporarily making the sample solution acidic with pH 4.5 or less or alkaline with pH 11 or higher, there can be used reagents which can make the PH range of sample solution as mentioned above and do not influence the analyte.

Examples of such reagents are buffer solutions such as glycine-hydrochloric acid, potassium phthalate-hydrochloric acid, citric acid-phosphoric acid, citric acid-sodium citrate, acetic acid-sodium acetate, succinic acid-sodium hydroxide, potassium phthalate-sodium hydroxide, glycine-sodium hydroxide, sodium carbonate-sodium hydrogen carbonate, sodium borate-sodium hydroxide, dimethylglutaric acid-tris(hydroxymethyl)aminomethane-aminomethylpropanediol (GTA), etc.; acids such as inorganic acids, e.g., hydrochloric acid, sulfuric acid, phosphoric acid, etc., organic acids, e.g. maleic acid, acetic acid, etc. alone or as a mixture thereof; alkalis such as inorganic bases, e.g. sodium hydroxide, potassium hydroxide, ammonia water, etc.; organic bases such as ethanolamine, etc., alone or as a mixture thereof.

The pH of the sample solution adjusted by using such a reagent is pH 4.5 or less or pH 11 or higher, more preferably pH 4 or less or pH 12 or higher in order to almost completely remove influences of complement components and the like.

As the reagent which changes the pH of the sample solution (reaction solution) to about neutral, it is preferable to use ones having buffering ability at near neutral. Preferable examples of such reagents are phosphoric acid and salts thereof, imidazole-hydrochloric acid, veronal-hydrochloric acid, tris(hydroxymethyl)aminomethane (Tris), or Good's buffers such as N-(2-acetamido)-2-aminoethanesulfonic acid (ACES), 3-morpholinopropanesulfonic acid (MOPS), N,N-bis(2-hydroxyethyl)-2-aminoethanesulfonic acid (BES), N-tris(hydroxymethyl)methyl-2-aminoethanesulfonic acid (TES), N-2-hydroxyethylpiperadine-N'-2-ethanesulfonic acid (HEPES), etc.

It is also possible to use the acids or alkalis as mentioned above.

After the above-mentioned pretreatment, the resulting sample solution is subjected to the measurement of the amount of analyte according to a conventional complement immunoassay using an immunoassay reagent composition comprising (i) liposomes fixing an antigen or antibody to analyte on surfaces of liposome membranes, encapsulating a detectable marker therein, and being susceptible to membrane lysing action by complement activity, and (ii) complement.

The liposomes used in the present invention can be prepared by conventional methods such as a voltexing method, a sonication method, a surfactant removal method, a reversed phase evaporation method (REV method), an ethanol infusion method, an ether infusion method, a pre-vesicle method, a French press extrusion method, a $Ca^{2+}$ fusion method, an annealing method, a freeze thawing method, a freeze drying method, a W/O/W emulsion method, etc., and methods such as a stable plurilamellar vesicle method (SPLV method) reported by S. M. Gruner et al. [Biochemistry, 24, 2833 (1985)], and a method using a lipopolysaccharide as one constituent of membrane and reported by some of the present inventors [Japanese Patent Unexamined Publication No. 63-107742 (=U.S. Pat. No. 4,861,597)].

As the main constituent of membrane of the liposome, there can be exemplified each or combinations of two or more of substances used as materials for membrane in preparation of conventional liposomes, i.e. natural lecithins (e.g. egg yolk lecithin, soybean lecithin, etc.), phospholipids such as dipalmitoylphosphatidylcholine (DPPC), dimyristoylphosphatidylcholine (DMPC), distearoylphosphatidylcholine (DSPC), dioleoylphosphatidylcholine (DOPC), dipalmitoylphosphatidylethanolamine (DPPE), dimyristoylphosphatidylethanolamine (DMPE), egg yolk phosphatidylglycerol, dipalmitoylphosphatidylglycerol (DPPG), dimyristoylphosphatidic acid (DMPA), dipalmitoylphosphatidic acid (DPPA), palmitoyloleoylphosphatidylcholine (POPC), etc. alone or as a mixture thereof; mixtures of these substances and cholesterols; and combinations of the mixtures mentioned above and lipopolysaccharides, etc.

Sensitization (fixation) of antigen or antibody on surfaces of liposome membranes can be carried out by conventional methods such as a crosslinking method (Biochemistry Vol. 20 (1981) 4229–4288; The Journal of Biological Chemistry Vol. 257 (1982) 286–288), a lipid activation method, etc.

As the crosslinking agents used in the crosslinking method, there can be used, for example, N-succinimidyl 3-(2-pyridyldithio)propionate (SPDP), N-succinimidyl 4-(p-maleimidophenyl)butyrate (SMPB), N-succinimidyl 4-(p-maleimidophenyl)acetate (SMPA), N-succinimidyl 4-(p-mateimidophenyl)propionate acetate (SMPP), N-(4-maleimidobutyryloxy)succinimide (GMBS), N-(6-maleimidocaproyloxy)succinimide (EMCS), etc.

The antibody used in the present invention wherein the analyte is an antigen is not critical, and any antibody can be used so long as it is an antibody to an analyte to be measured. That is, there may be used either polyclonal antibodies prepared by immunizing animals such as horse, cattle, sheep, rabbit, goat, rat, mouse, etc. with an analyte to be measured, according to a conventional method, for example, any of the methods described in Tadashi Matsuhashi et al. "Meneki Jikken-gaku Nyumon" 2nd. ed., Gakkai-Shuppan Center Ltd., 1981; and E. Harlow et al. "Antibodies" Cold Spring Harbor Laboratory, 1988, pp. 53–138, or monoclonal antibodies produced by Hybridomas obtained by fusing cells from a tumor line of mice together with mouse spleen cells previously immunized with an analyte to be measured, according to the conventional method, i.e., the cell fusion method established by G. K öhler and C. Milstein (Nature, 256, 495, 1975). These polyclonar and/or monoclonar antibodies may be used singly or in proper combination of two or more thereof. Needless to say, they may be used, if necessary, after digesting them with an enzyme such as pepsin or papain into $F(ab')_2$, Fab' or Fab.

The antigen used in the present invention wherein the analyte is an antibody is not critical, and any antigen can be used so long as it binds to the analyte.

As the marker encapsulated in the liposomes, any markers usually used in liposome immunoassay using complement can be used without particular limitation so long as they are detectable.

Examples of the markers are enzymes such as alkaline phosphatase, glucose-6-phosphate dehydrogenase (g6PDH), β-galactosidase, etc; coenzymes such as nicotinamide adenine dinucleotide (NAD), nicotinamide adenine dinucleotide phosphate (NADP), flavin adenine dinucleotide (FAD), etc.; substances which can emit fluorescence such as carboxyfluorescein, fluorescein isothiocyanate, fluorescein isocyanate, tetrarhodamine isothiocyanate, 5-dimethylamino-1-naphthalenesulfonyl chloride, etc.; luminescent substances such as luminol, isoluminol, luciferin, eosin Y, auramine O, bis(2,4,6-trichlorophenyl) oxalate, N-methylacridinium ester, etc.; dyes such as Arsenazo III, 4-(2-pyridylazo)resorcinol, 2-(5-bromo-2-pyridylazo)-5-(N-propyl-N-sulfopropyl)aminophenol sodium salt etc.; sugars such as glucose, etc.; ionic compounds such as potassium bichromate, sodium bichromate, sodium chloride, etc.; radical compounds such as nitroxide compounds; spin markers such as 2,2,6,6-tetramethylpiperidin-1-oxyl (TEMPO), etc.

The amount of the marker encapsulated in the liposomes changes depending on the kind of marker and is not limited particularly, so long as a sufficient difference is shown when the liposome membrane is lysed. For example, in the case of using glucose-6-phosphate dehydrogenase as the marker, there is prepared an enzyme solution, which is used as a solution containing a marker at the time of preparation of liposomes, in a concentration of usually 1000 to 5000 U/ml, preferably 2000 to 3000 U/ml.

Methods for measuring the amount of marker change depending on the kind of marker used. For example, when an enzyme is used as the marker, the marker can be measured according to the method, for example, described in T. Kitagawa, T. Nambara, A. Tsuji and E. Ishikawa: "Enzyme Immunoassay Methods", an extra issue No. 31 of Tanpakushitsu Kakusan Koso, pp. 51–63, Kyoritsu-Shuppan Ltd., published on Sep. 10, 1987. When a coenzyme is used as the marker, the measurement can be carried out, for example, as described in U.S. Pat. No. 4,704,355. When a substance emitting fluorescence is used as the marker, the measurement can be carried out, for example, as described in A. Kawano: "Zusetsu Keiko-Kotai" 1st. ed. Soft Science, Inc., 1983. When a luminescent substance is used as the marker, the measurement can be carried out, for example, as described in T. Kitagawa, T. Nanbara, A. Tsuji and E. Ishikawa: "Enzyme Immunoassay Methods", an extra issue No. 31 of Tanpakushitsu Kakusan Koso, pp. 252–263, Kyoritsu-Shuppan Ltd., published on Sep. 10, 1987. When a dye is used as the marker, the measurement can be carried out, for example, as described in Andrews, Janoff, et al.; Clin. Chem., vol. 29, p. 1587, 1983. When sugar is used as the marker, the measurement can be carried out, for example, as described in T. Kataoka, et al.: Eur. J. Biochem., vol. 21, p. 80, 1971. When an ionic compound is used as the marker, the measurement can be carried out, for example, as described in Y. Umezawa, et al.: Talamta, vol. 31, p. 375, 1984. When a radical compound is used as the marker, the measurement can be carried out, for example, as described in Wu R. Alving, et al.: J. Immunal Methods, vol. 9, p.165, 1975. When a spin marker is used as the marker, the measurement can be carried out, for example, as described in T. Kitagawa, T. Nanbara, A. Tsuji and E. Ishikawa: "Enzyme Immunoassay Methods", an extra issue No. 31 of Tanpakushitsu Kakusan Koso, pp. 264–271, Kyoritsu-Shuppan Ltd., published on Sep. 10, 1987.

The amount of liposomes immediately before the measurement (immunoassay) in terms of the phospholipid amount contained in the liposomes is usually 1 to 500 nmol/ml., preferably 5 to 100 nmol/ml.

As the analyte measurable according to the process of the present invention, there is no limitation thereto so long as an antibody or antigen to the analyte can be obtained by any methods. Examples of such analytes measurable according to conventional complement immunoassay methods are drugs having biological and clinical importance, metabolites, vitamines, insecticides, steroids, peptides, hormones, hepatitis markers, cancer markers, antibodies, serum proteins, etc. Concrete examples are as follows. Endocrine system relating substances:

thyroid stimulating hormone (TSH), growth hormone, somatomedin C, luteinizing hormone, follicle stimulating hormone, prolactin, adrenocorticotropic hormone, vasopressin, oxytocin, somatostatin, enkephalin, β-endorphin, thyroxine, triiodothyronine, thyroglobulin, anti-thyroglobulin antibody, anti-$T_4$ antibody, anti-$T_3$ antibody, anti-TSH antibody, calcitonin, catecholamine, dopamine, serotonin, parathyroid hormone, aldosterone, renin, angiotensin, contisol, cortisone, deoxycortisol, deoxycorticosterone, corticosterone, androsterone, progesterone, pregnenolone, estrogen, estrone, estradiol, estriol, testosterone; gonadotropin, insulin, anti-insulin antibody, C-peptide, glucagon, gastrin, secretin, cyclic AMP, cyclic GMP, prostaglandins, thromboxane, erythropoietin, histamine, etc. Tumor relating substances:

CEA, ferritin, $\beta_2$-microglobulin, elastase, α-fetoprotein, neural specific enolase, prostatic specific antigen, CA19-9, etc. Drugs and Vitamines:

phenobarbital, phenytoin, carbamazepine, primidone, ethosuximide, valproic acid, acetazolamide, sulthiame, glutethimide, clonazepam, nitrazepam, diazepam, pentobarbital, secobarbital, bupivacaine, mepivacaine, lidocaine, procainamide, quinidine, digoxin, digitoxin, theophylline, amitriptyline, imipramine, amikacin, gentamicin, tobramycin, cefalexin, sulfamethoxazole, methotrexate, cyclosporin, methylprednisolone, salicylic acid, acetaminophen, indomethacin, allopurinol, vitamin A, carotene, vitamin $B_1$, vitamin $B_2$, vitamin $B_6$, vitamin $B_{12}$, folic acid, folic acid, vitamin C, vitamin D, vitamin E, etc. Serum or plasma relating substances:

albumin, $\alpha_1$-microglobulin, $\alpha_1$-antitrypsin, $\alpha_2$-macroglobulin, haptoglobin, hemopexin, transferrin, myoglobin, IgG, IgM, IgA, IgD, IgE, fibrinogen, antithrombin, plasminogen, antiplasmin, protein C, theumatoid factor, anti-DNA antibody, C reactive protein, etc. Virus and infectious disease relating substances:

HBs antigen, HBs antibody, EBc antibody, HTLV-I antibody, HTLV-III antibody, TPHA, various virus antigens, various virus antibodies, etc.

As the complement used in the present invention, there can be used those obtained from blood of animals such as human being, guinea pig, horse, sheep, etc., and purified according to conventional methods, and those conventionally used.

The reagent composition for immunoassay of the present invention comprises (i) liposomes fixing an antigen or antibody to analyte on surfaces of liposome membranes, encapsulating a detectable marker therein, and being susceptible to membrane lysing action by complement activity, (ii) complement, and (iii) a reagent for making a sample solution acidic with PH 4.5 or less or alkaline with pH 11 or higher temporarily.

The reagent composition may further contain a free (not fixed) antigen or antibody to the analyte, a substrate in the case of using an enzyme as the marker, and conventional additives.

It is also possible to add to the measuring system according to the present invention additives conventionally used in this field such as proteins, e.g. bovine serum albumin (BSA), gelatin, etc., sugars, chelating agents, reducing agents, antiseptics, etc.

The using amounts of various reagents, the amount of substrate in the case of using an enzyme as the marker, the concentrations of various additives mentioned above, can be selected suitable from the ranges conventionally used in the conventional complement immunoassay methods.

The process of the present invention can be applied not only to manual methods but also to measuring systems using autoanalyzers so as to carry out the measurement easily and rapidly. There is no particular limitation to combinations of reagents in the case of measurements using autoanalyzers. Needless to say, the best combination of reagents can be selected taking other factors into consideration.

The present invention is illustrated by way of the following Experimental Examples and Examples.

EXPERIMENTAL EXAMPLE 1

(1) Preparation of phenytoin sensitized liposomes

Liposomes encapsulating glucose-6-phosphate dehydrogenase (G6PDH) and having phospholipid derivative of phenytoin (antiepileptic) as membrane component were prepared by the voltexing method as follows.

First, 72 μmol of dimyristoylphosphatidylcholine, 8 μmol of dimyristoylphosphatidylglycerol, 80 μmol of cholesterol and 0.8 μmol phosphatidylethanolamine derivative of phenytoin were dissolved in 5 ml of chloroform and dried under reduced pressure. To this, 7.5 ml of 10 mM Tris/HCL buffer (pH 7.8) dissolving G6PDH so as to make 2500 μ/ml was added and mixed in a voltex mixer. The thus obtained lipid hydration solution suspending liposomes therein was subjected to particle size control by passing through a membrane filter having a pore size of 0.2 μm. Then, the enzyme not encapsulated by the liposomes was removed by repetition of ultracentrifugation (100,000×g). The finally obtained liposomes were suspended in 0.1M Tris/HCl buffer solution (pH 7.8) and stored in a refrigerator.

(2) Influence of pH on complement activity

Influence of pH on liposome membrane lysing reaction caused by complement component and the like contained in a sample was examined by using the G6PDH-encapsulating phenytoin sensitized liposomes prepared in (1).

To each 20 μl of fresh human serum, 200 μl of 25 mM GTA buffer solution adjusted to pH 1 to 13, respectively, was added. After treating at 37° C. for 5 minutes, 200 μl of 0.25M Tris/HCl buffer solution contain a sufficient amount of rabbit anti-phenytoin antibody and G6PDH-encapsulating phenytoin sensitized liposomes (lipid concentration 5 nmol/ml) was added to the thus treated solution and adjusted to pH 8. After reacting at 37° C. for 5 minutes, G6PDH activity released by the liposome membrane immunolysing reaction was measured from absorbance changes at 340 nm of NADH using glucose-6-phosphate (G6P) and NAD as substrates to obtain complement residual activity values in the samples.

The results are shown in FIG. 1. In FIG. 1, the complement residual activity values are shown as relative values taking the absorbance of the sample (fresh human serum) treated with GTA buffer solution having a pH 8 as 100.

As is clear from FIG. 1, in the case of serum sample, the sample itself contains a component having complement activity to express liposome membrane lysing action. But this activity was able to be reduced by making the sample solution acidic or alkaline temporarily. When the pH was made 4.5 or less, or 11 or higher, the complement activity was reduced to 60% or less. Further, it was found that when the pH was made 4 or less, or 12 or higher, the influence of complement in the sample was almost completely removed.

Example 1

(1) Preparation of phenobarbital sensitized liposomes

The phenobarbital sensitized liposomes were prepared in the same manner as described in Experimental Example 1 (1) except for using a phospholipid derivative of phenobarbital in place of phosphatidylethanolamine derivative of phenytoin.

(2) Measurement of phenobarbital concentration in serum

After mixing 200 μl of a serum sample obtained from a patient administrated with phenobarbital (antiepileptic) and 200 μl of 0.3N hydrochloric acid, the sample was treated under acidity (pH 1) for 5 minutes. To the thus treated sample solution in an amount of 6 μl, 200 μl of buffer solution (pH 6.0) containing rabbit anti-phenobarbital antibody and enzyme substrate (6 mM NAD, 16 mM G6P) was added and reacted at 37° C. for 5 minutes. To this, 200 μl of 30 mM Tris/HCl buffer solution (pH 8.5) containing phenobarbital sensitized G6PDM-encapsulating liposomes (lipid concentration 5 nmol/ml) and guinea pig complement (20 $CH_{50}$/ml) was added and reacted at 37° C. for 5 minutes. Activity value of G6PDH released from the liposomes by the liposome membrane lysing action by the complement was obtained by measuring absorbance at 340 nm by NADH to give the amount of phenobarbital.

The results are shown in Table 1. In Table 1, the control sample is pool serum wherein complement activity is already inactivated, and the interfering substance-containing sample is a serum sample containing measurement interfering substances (one having complement activity and complement controlling factors disclosed, e.g., in "Immunochemistry: An Advanced Textbook" ed. L. E. Glynn and M. W. Steward, p. 368, John Wiley & Sons, 1977).

TABLE 1

| | Complement immunoassay | | |
|---|---|---|---|
| Sample | HCl non-treating method (prior art) (PB; μg/ml) | HCl treating method (present invention) (PB; μg/ml) | EIA method (PB; μg/ml) |
| Control 1 | 20.1 | 19.6 | 18.8 |
| " 2 | 27.9 | 29.9 | 32.6 |
| " 3 | 29.9 | 31.0 | 30.0 |
| Sample No. 1 | 88.9 | 16.5 | 18.6 |
| (containing 2 | 51.1 | 13.8 | 13.6 |
| interference | | | |
| substance) 3 | 4.7 | 3.1 | 2.9 |
| 4 | 20.2 | 6.7 | 5.1 |
| 5 | 96.6 | 25.8 | 24.5 |
| 6 | 22.2 | 31.0 | 30.3 |
| 7 | 17.7 | 31.5 | 31.1 |
| 8 | 10.2 | 7.9 | 7.0 |
| 9 | 7.0 | 5.1 | 4.8 |
| 10 | 1.9 | 0.1 | 0.1 |

As is clear from Table 1, when the interfering substance is present in the samples, influences of the interfering substance in the samples are exhibited in the prior art complement immunoassay wherein no hydrochloric acid treatment is conducted to show remarkable differences between the measured values comparing with the EIA method. In contrast, according to the process of the present invention wherein the hydrochloric acid treatment is conducted, the measured values are very close to those obtained by the EIA method. Thus, a precise measurement becomes possible by the present invention.

Example 2

Measurement of phenytoin concentration in serum (1) Preparation of phenytoin sensitized liposomes The phenytoin sensitized liposomes were prepared in the same manner as described in Experimental Example 1 (1).

(2) Measurement of phenytoin concentration in serum

To 3 μl of serum obtained from a patient administrated with phenytoin (antiepileptic), 200 μl of a buffer solution (pH 4) containing rabbit anti-phenytoin antibody and enzyme substrate (6 mM NAD, 16 mM G6P) was added and treated at 37° C. for 5 minutes for carrying out the reaction. To this, 200 μl of 30 mM Tris/HCl buffer solution (pH 8.5) containing phenytoin sensitized G6PDE-encapsulating liposomes (lipid concentration 5 nmol/ml) and guinea pig complement (20 $CE_{50}$/ml) was added to make the pH 7.8, followed by reaction at 37° C. for 5 minutes. Enzyme activity value of released G6PDH was obtained by measuring absorbance at 340 nm of NADE. The phenytoin amount in the sample was calculated and compared with the phenytoin concentration in the serum measured by the EIA method.

Figure 2:
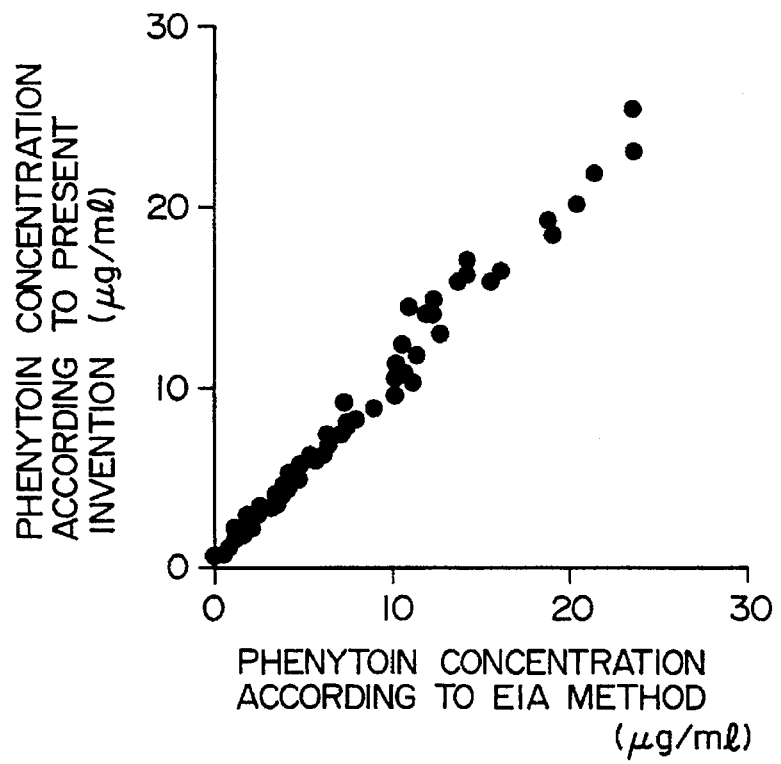
FIG. 2 is a graph showing a correlation between the serum phenytoin concentration obtained by the process of the present invention and that obtained by the EIA method.

The results are shown in FIG. 2.

Figure 3:
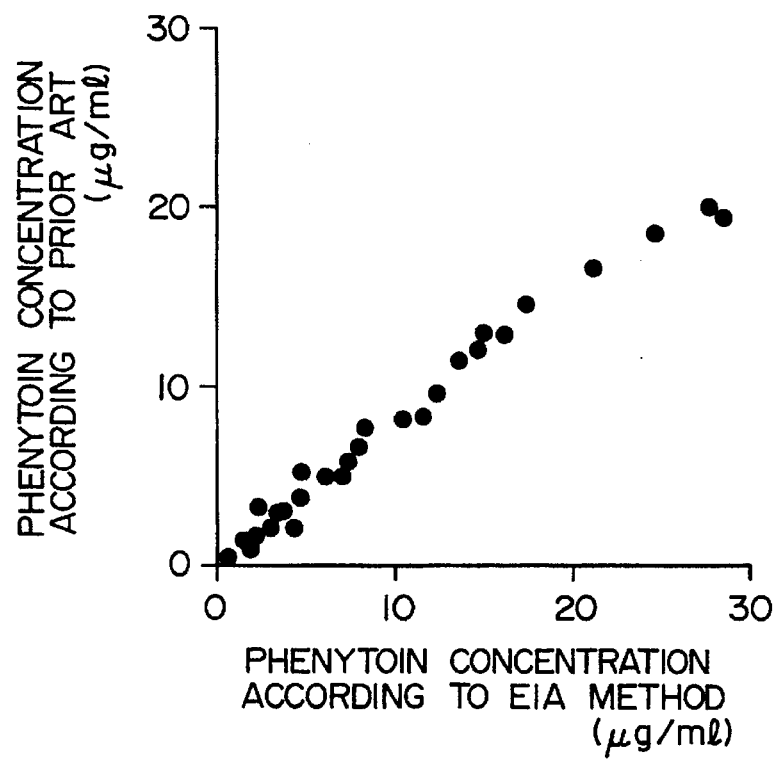
FIG. 3 is a graph showing a correlation between the serum phenytoin concentration obtained by a prior art method (in a liposome immunoassay, serum phenytoin concentration being measured at pH 6) and that obtained by the EIA method.

On the other hand, the results obtained by not conducting the acid treatment and measuring at pH 6 as control are shown in FIG. 3.

In FIG. 3, the number of samples is 30, $\gamma=0.984$ and $Y=0.697\times+0.60$. In FIG. 2, the number of samples is 79, $\gamma=0.993$ and $Y=1.017\times-0.35$.

As is clear from the above results, by making the samples acidic temporarily according to the present invention, influences of the interfering substance present in the samples can be removed. Thus, the correlation with other complement immunoassay methods can be improved.

As mentioned above, by making the sample solution temporarily acidic with pH 4.5 or less, or alkaline with pH 11 or higher, followed by changing the pH of the sample solution to about neutral before the measurement of analyte amount in the sample, the influences of complement components and the like present in the sample in the complement immunoassay using serum or plasma as the sample can be removed. Thus, analyte antigen or analyte antibody in the sample can be determined precisely according to the present invention. Further, according to the present invention, the line treatment in autoanalyzers becomes possible in contrast to prior art heat treating method. Thus, excellent effects such as improvement in precision, speed-up and energy saving in the immunoassay using liposomes are shown in the present invention.

What is claimed is:

1. An immunoassay method for determining the amount of an analyte in a sample comprising the steps of:

(i) preparing a reagent composition comprising:
   (a) liposomes, wherein an antigen or antibody which binds said analyte to be measured are fixed on membrane surfaces of said liposomes, a detectable marker is encapsulated therewithin, and wherein said liposomes are susceptible to membrane lysing action by complement activity, and
   (b) complement;

(ii) acidifying the sample to pH 4.5 or lower with one or more reagents selected from the group consisting of glycine-hydrochloric acid, potassium phthalate-hydrochloric acid, citric acid-phosphoric acid, citric acid-sodium citrate, acetic acid-sodium acetate, succinic acid-sodium hydroxide, potassium phthalate-sodium hydroxide, hydrochloric acid, sulfuric acid, phosphoric acid, maleic acid and acetic acid;
   to remove influences caused by interfering substances present in the sample so as to not affect the measurement of the analyte or the reagent composition, and (iii) adjusting the pH of the sample to about neutral prior to or at the time of adding the reagent composition, and (iv) contacting said reagent composition with said sample and measuring the amount of detectable marker released from said liposomes to determine the analyte in the sample.

2. An immunoassay method for determining the amount of an analyte in a sample comprising the steps of:

(i) preparing a reagent composition comprising:
   (a) liposomes, wherein an antigen or antibody which binds said analyte to be measured are fixed on membrane surfaces of said liposomes, a detectable marker is encapsulated therewithin, and wherein said liposomes are susceptible to membrane lysing action by complement activity, and (b) complement;

(ii) alkalinizing the sample to pH 11 or higher to remove influences caused by interfering substances present in the sample so as to not affect the measurement of the analyte, and (iii) adjusting the pH of the sample to about neutral prior to or at the time of adding the reagent composition, and (iv) contacting said reagent composition with said sample and measuring the amount of detectable marker released from said liposomes to determine the analyte in the sample.

3. The immunoassay method according to claim 2, wherein the alkalinization is carried out using a buffer solution, an inorganic base, an organic base, or a mixture thereof.

4. The immunoassay method according to claim 2, wherein the alkalinization is carried out using one or more reagents selected from the group consisting of glycine-sodium hydroxide, sodium carbonate-sodium hydrogen carbonate, sodium borate-sodium hydroxide, dimethylglutaric acid-tris(hydroxymethyl)aminomethane-aminomethylpropanediol (GTA), sodium hydroxide, potassium hydroxide, ammonia water and ethanolamine.

* * * * *